United States Patent
Edwards et al.

(10) Patent No.: US 9,709,514 B2
(45) Date of Patent: Jul. 18, 2017

(54) X-RAY BACKSCATTER SYSTEM AND METHOD FOR DETECTING DISCREPANCIES IN ITEMS

(75) Inventors: William Talion Edwards, Foristell, MO (US); Gary E. Georgeson, Tacoma, WA (US); James E. Engel, Newport Beach, CA (US)

(73) Assignee: THE BOEING COMPANY, Chicago, IL (US)

( * ) Notice: Subject to any disclaimer, the term of this patent is extended or adjusted under 35 U.S.C. 154(b) by 571 days.

(21) Appl. No.: 13/437,459

(22) Filed: Apr. 2, 2012

(65) Prior Publication Data
US 2013/0255385 A1    Oct. 3, 2013

(51) Int. Cl.
G01N 23/00    (2006.01)
G01N 23/203    (2006.01)

(52) U.S. Cl.
CPC ..... *G01N 23/203* (2013.01); *G01N 2223/426* (2013.01); *G01N 2223/631* (2013.01); *G01N 2223/6466* (2013.01); *G01N 2223/652* (2013.01)

(58) Field of Classification Search
CPC .............. G01N 23/203; G01N 2223/053
USPC ............................ 378/70, 86, 87
See application file for complete search history.

(56) References Cited

U.S. PATENT DOCUMENTS

| | | | |
|---|---|---|---|
| 6,421,418 B1 * | 7/2002 | Schulte | 378/89 |
| 6,563,906 B2 | 5/2003 | Hussein et al. | |
| 7,203,276 B2 | 4/2007 | Arsenault et al. | |
| 7,463,714 B2 | 12/2008 | Edwards et al. | |
| 7,508,910 B2 | 3/2009 | Safai et al. | |
| 7,623,626 B2 | 11/2009 | Safai et al. | |
| 7,649,976 B2 | 1/2010 | Georgeson et al. | |
| 7,983,387 B1 | 7/2011 | Toh et al. | |
| 8,033,724 B2 | 10/2011 | Edwards et al. | |
| 8,094,781 B1 | 1/2012 | Safai et al. | |
| 2006/0245548 A1 * | 11/2006 | Callerame | G01N 23/203 378/160 |
| 2008/0095310 A1 * | 4/2008 | Edwards et al. | 378/57 |
| 2008/0229834 A1 * | 9/2008 | Bossi et al. | 73/627 |
| 2009/0133501 A1 * | 5/2009 | Georgeson | 73/632 |
| 2010/0319455 A1 * | 12/2010 | Ihn | 73/603 |

OTHER PUBLICATIONS

Bossi, R.H. et al., X-ray Backscatter Imaging With a Spiral Scanner.
Herr, Michael D. et al., A Flying Spot X-Ray System for Compton Backscatter Imaging; IEEE Transactions on Medical Imaging, vol. 13, No. 3, Sep. 1994.
Mullin, S .K. et al., A compton-scatter spectrometry technique for flaw detection; Nuclear Instruments and Methods in Physics Research A 353 (1994) 663-667.
Towe, Bruce C. et al., X-Ray Backscatter Imaging; IEEE Transactions on Biomedical Engineering, vol. BME-28, No. 9, Sep. 1981.

* cited by examiner

*Primary Examiner* — Dani Fox

(57) ABSTRACT

A method for detecting discrepancies in an item is provided. The method comprises: directing energy waves at the item along at least one dimension, wherein a portion of the energy waves are reflected back from the item; detecting reflected energy waves from the item along at least one dimension and recording the intensity of the detected reflected energy waves, and forming a one-dimensional image of the item from the detected reflected energy waves.

14 Claims, 3 Drawing Sheets

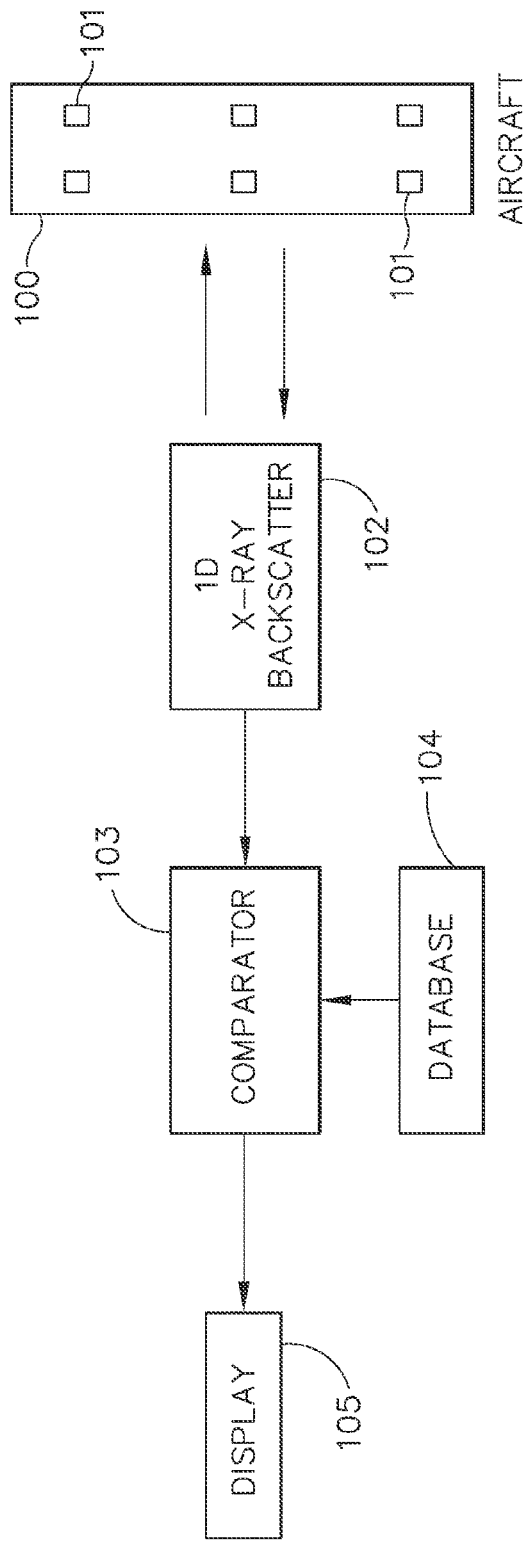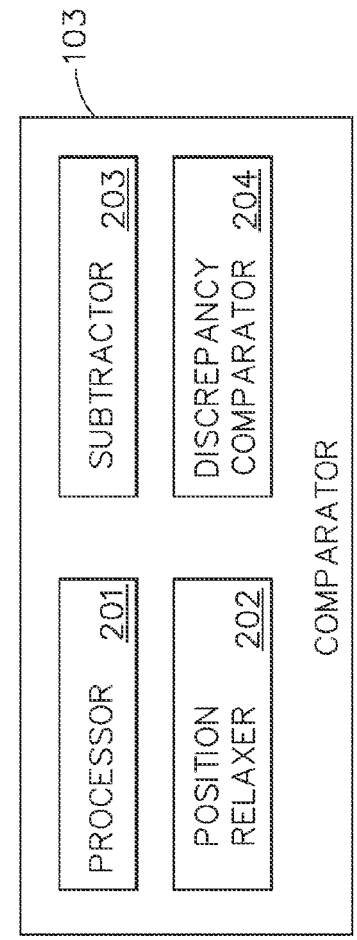

X-RAY BACKSCATTER SYSTEM AND METHOD FOR DETECTING DISCREPANCIES IN ITEMS

BACKGROUND

Foreign objects are often introduced inside commercial and military aircraft during manufacturing or modifications. Items such as tools, fasteners, drill shavings, manufacturing material, personal objects, and debris may be inadvertently left inside the aircraft once the manufacturing or modification is complete.

For example, when co-drilling aircraft skins with their mating backing structure during manufacturing, foreign objects in the form of drill shavings are produced. Due do the forces from the drilling operations and due to the tendency for the chips to fall to the floor, drill shavings can potentially fall into gaps between the skin and the backing structure. It is often desirable to install fasteners into the newly drilled holes while the components are still held together in the drilling machine. Because of the potential presence of the stray drill shavings, the fasteners cannot be installed until an inspection is performed to ensure no foreign object debris (FOD) is present in the interface between the skin and the backup structure.

Moreover, during the skin installation operation of many aerospace structures, temporary fasteners are typically used to hold the skin to underlying ribs during fastener installation. If the operation is performed incorrectly, the holes in the underlying structure and skin can be misaligned, resulting in drilling or reaming of the hole which subsequently causes it to become oversized. Oversized holes reduce the intended properties of the fastened structure and may even produce accelerated in-service damage. This unfortunate opportunity also exists during original maintenance of the aircraft.

The presence of FOD in an aircraft is undesirable. FOD may interfere with the proper operation of critical aircraft systems. For example, FOD may foul cables or other mechanical devices that are used to control flight surfaces. FOD may also cause electrical shorts. Drill shavings can also cause discrepancies between structural surfaces, thereby increasing localized stresses and leading to crack sites or corrosion start points. Such undesirable effects of FOD may be costly and dangerous. It may inhibit proper operation of the aircraft to the point of causing a failure. Accordingly, during manufacturing operations the structure may have to be disassembled and time-consuming visual inspection performed in order to see if any FOD is present and often times no FOD is found or it is only found in very limited areas.

According to contemporary practice, for example as set forth in U.S. Pat. No. 7,463,714, technicians may inspect work areas of aircraft with two-dimension (2D) and/or three-dimension (3D) X-ray backscatter systems. Such systems are however expensive and usually produce large amount of data to be processed in order to identify FOD or other discrepancies in the aircraft.

As a result, it would be desirable to have a system for identifying FOD or other discrepancies in the aircraft which is not as expensive as, and/or produces data faster than contemporary two-dimension (2D) and/or three-dimension (3D) X-ray backscatter systems.

SUMMARY

In one aspect a method for detecting discrepancies in an item is provided. The method comprises: directing energy waves at the item along at least one dimension, wherein a portion of the energy waves are reflected back from the item; detecting reflected energy waves from the item along at least one dimension and recording the intensity of the detected reflected energy waves, and forming a one-dimensional image of the item from the detected reflected energy waves In another aspect, a system for detecting discrepancies in an item is provided. The system comprises: an emitter for emitting energy waves at the item, wherein a portion of the emitted energy waves are reflected back from the item as reflected energy waves; a detector for detecting the reflected energy waves from the item, and an image-former for forming a one-dimensional image of the item from detected reflected energy waves.

In a further aspect, a system for detecting discrepancies in an item is provided. The system comprises: an X-ray emitter for emitting X-rays at an item, wherein a portion of the emitted X-rays are reflected back from the item; a one-dimensional backscatter X-ray detector for detecting X-rays reflected back from the item along one dimension, and an image processor for generating a one-dimensional image from the detected X-rays backscattered from the item.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1 illustrates a block diagram showing an example discrepancy detector.

FIG. 2 shows a block diagram illustrating the comparator of FIG. 1 in greater detail.

DETAILED DESCRIPTION

Figure 3:
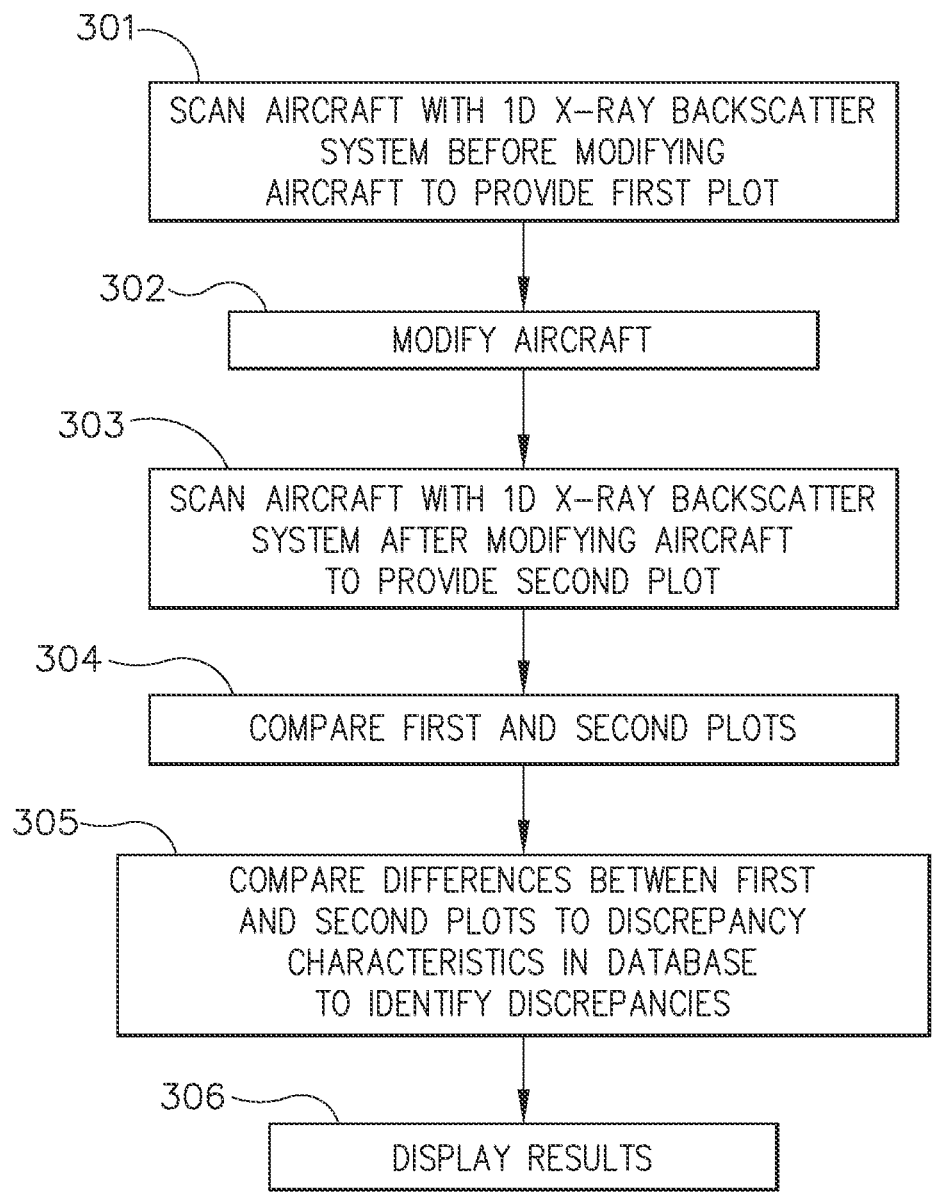
FIG. 3 shows a flow chart illustrating an example production flow comprising discrepancy accounting and detection.

Methods and systems are disclosed herein to provide for the detection of discrepancies in items such as aircraft, automobiles, ships, submarines, satellites, spacecraft, buildings, bridges, and pipelines with one-dimensional imaging. In one aspect, a method for detecting discrepancies in an item is provided. Energy waves, such as electromagnetic waves or stress waves, are directed at the item along at least one dimension. Energy waves reflected back from the item are detected along at least one dimension. As intended herein, the term "reflected energy waves" is meant to also include energy waves coming from below the surface of the item, such as backscattered X-rays. In addition, or alternatively, energy waves transmitted through the item may be detected, for instance when access to the side of the item opposite that facing the source of the energy waves is available.

The detected wave intensities are then used to form a one-dimensional (1D) image of the item establishing a correspondence between points along the dimension and the energy wave intensities detected at each point. For example, the one-dimensional image of the item may be a detected wave intensity plot, and wave intensities may be plotted against the positions on an axis along which the item was scanned. The methods and systems disclosed herein require simpler hardware and produce a faster data collection speed than previously used two-dimension and three-dimension approaches.

In some cases, discrepancies may be readily identified as spikes or troughs on an otherwise linear detected wave intensity plot. In this instance, the baseline of the plot itself serves as a reference for identifying discrepancies. In other cases, a reference image, such as a reference plot, may aid in the detection of discrepancies. A reference plot may be a plot taken by scanning the item prior to the item undergoing a modification procedure. In some cases, the reference plot is a model-based prediction of a plot of an item without discrepancies, where the model may be, for instance, a computer-aided design (CAD) model. One or more fiducials may also be attached to the item prior to scanning in order to facilitate registering the plot with respect to the reference plot. In this manner, processing of the images may be more readily facilitated.

Once the plots are registered, the plot of the item and the reference image may be compared in order to find discrepancies. The comparison may include, for example, a visual comparison of the plots. In order to more readily determine the differences between the plots, image subtraction may be applied where the intensity of each point of a reference plot is subtracted from that of the corresponding point of a plot taken after the item has been subjected to a modification procedure, thereby yielding a subtracted plot.

The plot of the item and/or the reference plot may be processed prior to comparing one to the other. Processing may render the plot of the item and the reference plot more alike one another while preserving information regarding the presence of any discrepancy. For example, such processing may comprise scaling the plot and/or the reference plot.

Portions of the plot of the item or of a subtracted plot may be compared to or checked against other plots and/or known characteristics of discrepancies. Such plots and characteristics may be stored in a database. In this manner, the identity of discrepancies may potentially be more readily determined. Characteristics of known FOD, for example, may be compared to increases in reflected wave intensity suspected to be due to FOD. This may be applied to other types of discrepancies; for example, a negative contribution to a plot may be compared with decreases in detected reflected waves due to cracks and/or gaps of known geometry and/or size.

The choice of energy waves to direct at the item will vary depending on, among other factors, the nature of the item and the materials it incorporates as well as the type of the discrepancies detected. Example energy waves include electromagnetic waves, such as infrared (IR), visible, ultraviolet, X-rays, and gamma rays as well as mechanical waves such as stress waves, for example sonic and ultrasonic waves. In some cases, the energy waves directed at the item may be able to penetrate at least one layer of the item. For example, when searching for drilling chips before riveting an aircraft panel, energy waves capable of penetrating the panel may be used. This way, the waves may be able to reach and reflect from objects interposed behind the panel, such as drilling chips.

The penetration of at least one outer layer of an item may be accomplished, for example, by directing X-rays at the item. An X-ray detector, for instance a large area detector, is used to detect X-rays reflected from the item, for example by Compton scattering. If an object is interposed between the outer layer and other parts of the item, for instance a second, inner or bottom layer, this will result in additional X-ray backscattering due to the presence of the object and therefore in an increase in the intensity of the X-rays detected by the detector.

As an example, an X-ray fan beam, such as that emitted by an X-ray tube with a rectangular emission slit, may be directed at an oil pipeline with the narrow beam-width in a direction parallel to the pipeline length. X-rays backscattered by the section of the pipeline invested by the beam may be detected with a large area detector that yields a detected backscattered X-ray intensity reading. Accordingly, an increase in backscattered X-rays will result in a higher reading by the detector, and vice versa.

A plurality of readings along the length of the pipeline may be taken, for example by scanning a system comprising an X-ray emitter and detector along the length of the pipeline. A plot of the detected backscattered X-ray intensity for a desired portion of the pipeline may thus be obtained. Changes in the plot intensity may then be diagnostic of amounts of corrosion sufficient to change the intensity of backscattered X-rays. Changes in the plot expected to occur because of known changes in the pipeline, such as changes in thickness at a junction, may be ignored as being due not to discrepancies, but to known features of the pipeline instead.

Figure 4:
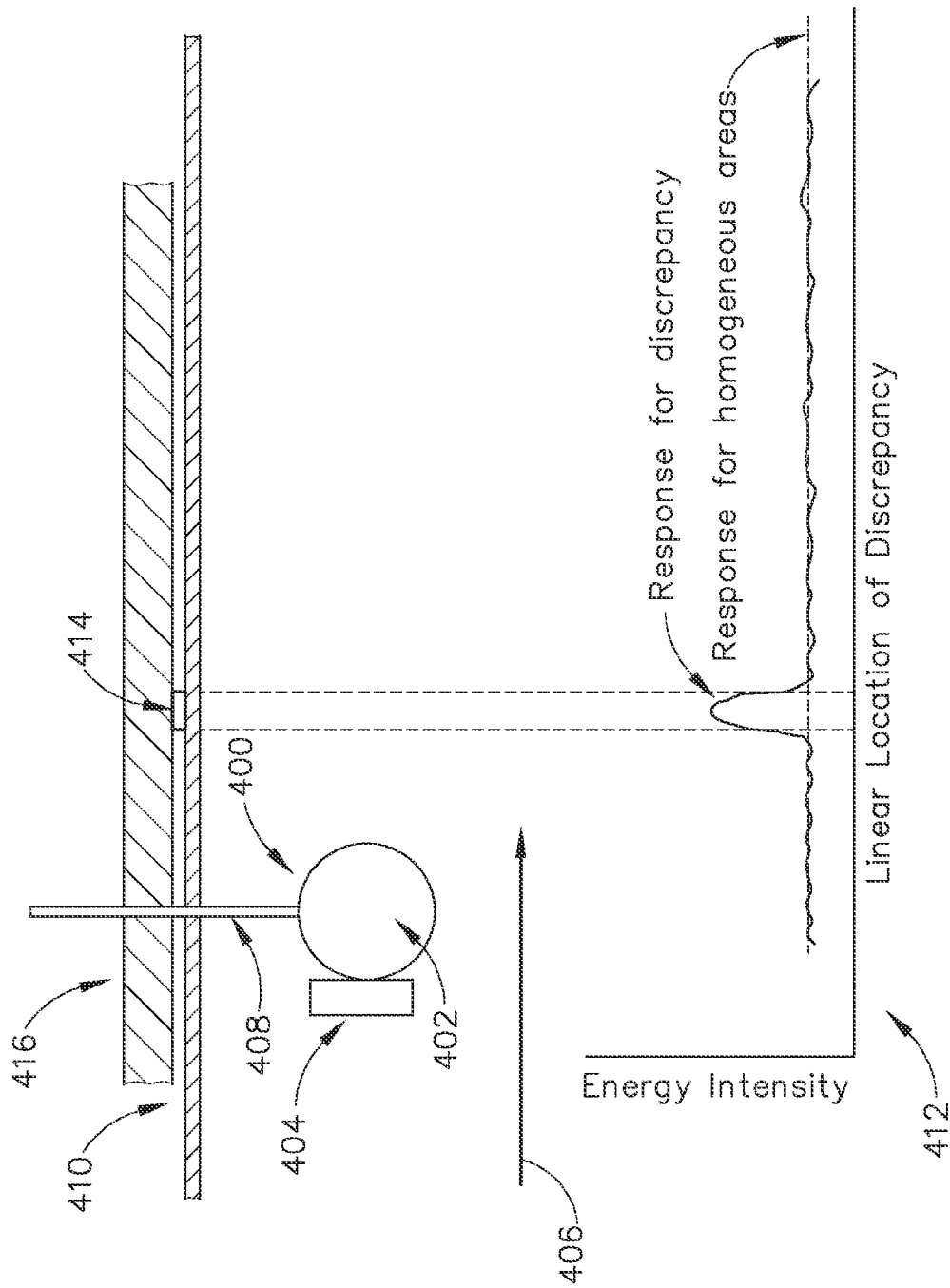
FIG. 4 illustrates an example detection of discrepancies behind the skin of an aircraft.

In another example, the X-ray beam and detector may be used to detect discrepancies that can occur during the manufacturing and maintenance of items. In the manufacturing of aircraft, for instance, typical discrepancies include foreign object debris (FOD) such as drill shavings, oversize holes, damaged spars, damaged ribs corrosion, cracks, gaps, and distortions. As described above, the method may be applied to detect whether drill shavings are left inside the hull of an aircraft. For instance, and as illustrated in FIG. 4, a one-dimension X-ray scanner assembly 400, comprising X-ray tube 402 and detector 404, may be scanned along the direction indicated by arrow 406. X-ray fan beam 408 penetrates the skin of the aircraft 410, and the intensity of backscattered X-ray waves is measured with detector 404, yielding plot 412. The presence of a discrepancy, such as drill shaving 414 interposed between skin 410 and internal structure 416, will appear as a spike in detected backscattered X-ray intensity.

In another aspect, a system for detecting discrepancies in an item is provided. The system comprises an emitter for emitting energy waves at the item, a detector for detecting energy waves reflected from the item, and an image-former for forming a one-dimensional image of the item from detected reflected energy waves. The system may also feature a comparator for comparing the one-dimensional image of the item with a reference image in order to facilitate the identification of any discrepancies that may exist in the item.

The emitter may be configured to emit, for example, electromagnetic waves, such as infrared (IR), visible, ultraviolet, X-rays, and gamma rays as well as mechanical waves such as stress waves. The detector is usually configured to detect waves of the same energy magnitude as those produced by the emitter. Accordingly, if the emitter emits X-rays, an X-ray detector may be used to detect X-rays backscattered from the item. It is to be understood, however, that the frequency of the backscattered X-rays need not to be the very same of those produced by the emitter, and that changes in frequency associated with the reflection of energy waves are to be expected and, if needed, taken into account.

The image former may be configured to form one-dimensional images, such as detected wave intensity plots. For example, the image former may take the output of a one-dimensional X-ray backscatter scanner and produce detected backscattered X-ray intensity plots. In this instance, the emitter may emit an X-ray fan beam, and the detector may be a one-dimensional X-ray backscatter scanner. The emitter and detector may be part of a scanner assembly that is moved along while scanning a region to be scanned, where the motion of the scanner assembly may be aided, for example, by a dedicated railing. The image former may comprise a computer readable memory medium stored in the system and a processor operable to access from the computer readable memory medium program instructions executable by the processor to form images from the output of the detector.

The comparator may be configured to compare the differences between a detected backscattered X-ray intensity plot of the scanned region taken prior to modification procedure, and a plot taken after the procedure. The comparison may be configured to compare the plots via intensity subtraction, thereby yielding a subtraction plots. In this manner, contributions due to suspected discrepancies may appear on the subtraction plots as increases or decreases in backscattered X-ray intensity. The comparator may comprise a computer readable memory medium stored in the system and a processor operable to access from the computer readable memory medium program instructions executable by the processor to compare images.

To aid in the identification of suspected discrepancies, portions of an image may be compared to or checked against other images and/or known characteristics of discrepancies. To this end, the system may be provided with a database of known discrepancies. For example, a negative contribution to an image may be compared with decreases in detected reflected waves due to oversize holes, cracks and/or gaps of known geometry and/or size.

EXAMPLES

FIG. 1 illustrates a flow chart of an example discrepancy detection system. An object, such as an aircraft 100, may be fitted with one or more fiducials 101. Typically, a plurality of fiducials 101 will be attached to aircraft 100. For example, fiducials 101 may be either temporarily or permanently attached to aircraft 100. The may be either inside, outside, or any combination of inside and outside the aircraft 100. Fiducials 101 may be located in a manner that facilitates enhanced alignment of X-ray backscatter images of the aircraft 100 or at least a portion thereof.

Fiducials 101 may be attached to aircraft 100 in a manner that assures that fiducials 101 remain in place throughout modification of aircraft 100. For example, fiducials 101 may be attached to aircraft 100 via adhesive bonding, such as via superglue, dental cement, or epoxy. As a further example, fiducials 101 may be attached to aircraft 100 via fasteners, such as bolts or screws.

Fiducials 101 facilitate alignment of images that are used to detect the presence of FOD and other discrepancies, as discussed in detail below. The use of fiducials 101 is optional. Other means for aligning the images may alternatively be used. For example the aligning may be based on known locations of spars and ribs. Alternatively, an encoding scheme may be used whereby a linear motion device is encoded so that an imaging sequence can be repeated. This may be carried out with, for example, linear rails, or with a robot that allows additional degrees of freedom for repeated scans.

A one-dimensional X-ray backscatter device 102 may be used to form images, such as detected backscattered X-ray intensity plots, that are used to determine the potential presence of FOD in aircraft 100 after modification thereof. An example one-dimensional X-ray backscatter device may include an X-ray emitter that emits an X-ray fan beam, e.g. an X-ray tube with a rectangular slit, and a large area detector for detecting the intensity of backscattered X-rays.

In order to facilitate the identification of discrepancies, an image taken after modification of an aircraft 100 may be compared to an image taken prior to modification, for example by showing both images on display 105. Optionally, the image taken after modification of aircraft 100 is compared to the image taken prior to modification of aircraft 100 by a comparator 103, for example by intensity subtraction. In this instance, the intensity of each point of a detected backscattered X-ray intensity plot taken prior to modification of aircraft 100 may be subtracted from that of a corresponding point of a plot taken after modification of aircraft 100 to provide a subtraction image. The subtraction image may thus be a subtraction plot that contains differences between the two plots. Such differences may be due to the presence to discrepancies, such as FOD, in aircraft 100.

Optionally, a database 104 containing characteristics of known (previously identified and characterized) discrepancies may be used to attempt to identify any potential discrepancies in the subtraction image. For example, the response of potential FOD in the subtraction image may be compared to that of known FOD in database 104 to attempt to determine if the potential FOD is actually FOD. The response on a subtraction plot associated with an object may depend on such geometric characteristics that may include size (such as largest dimension), shape, volume, key dimensions, ratios of dimensions, and/or the presence of unique structures.

A subtraction image, together with information representative of that provided by the subtraction image (which may be in a graphic or text format), and/or information resulting from use of database 104, may also be displayed on display 105. For example, the results may indicate that suspected drilling shavings may be present in the structure. As discussed above, the presence of such FOD may present a substantial hazard.

FIG. 2 shows comparator 103 in further detail. Comparator 103 may comprise a processor 201, a position relaxer 202, a subtractor 203, and/or a discrepancy comparator 204. Processor 201, position relaxer 202, subtractor 203, and/or discrepancy comparator 204 may be implemented either in hardware (such as via dedicated circuitry) or in software (such as via a general purpose microprocessor), or in any combination of hardware and software.

Processor 201 may perform processing tasks such as scaling X-ray intensity plots. Position relaxer 202 may vary, to some degree, the size, shape, and/or position of features of the image taken before modification and/or the image taken after modification, so as to better facilitate a match of such images by comparator 103. In this manner, minor differences between the two images are less likely to result in contributions to the subtraction image. Such minor differences may result from thermal expansion, mechanical stress, and/or movement of non-rigid components (cables, wiring, plumbing, etc.). Thus, the use of position relaxer 202 makes it more likely that items that appear in the subtraction image will be discrepancies, and it thus may reduce the occurrence of false positives.

As discussed above, subtractor 203 performs image subtraction to provide the subtraction image. For example, when the images are detected wave intensity plots, the intensity of each point of one of the plots is subtracted from that of a corresponding point of the other plot. However, the use of position relaxer 202 may result in the intensity of points being subtracted from that of other, generally nearby, points instead. In any event, position relaxer 202 attempts to cause a structure in one image to be subtracted from the same structure in another image even though the structure is not represented by the same points in each image.

Discrepancy comparator 204 compares the characteristics of items found in the subtraction image to characteristics of known discrepancies using database 104. For instance, oversize holes, cracks, or other structural defects may be given priority during this comparison.

FIG. 3 shows an example flow chart. Fiducials may be attached to the aircraft 100 prior to scanning. The aircraft may then be scanned with a one-dimensional X-ray backscatter scanner, as indicated in block 301. After this initial scanning, the aircraft may be modified as indicated in block 302. Then, the aircraft is again scanned, for example using the same equipment and procedure used for the initial scan, as indicated in block 303.

The two X-ray intensity plots resulting from the two scans may be compared as indicated in block 304, for example by subtraction. In some cases, more than one initial plot and more than one final plot may be necessary, depending upon the size of the area modified and the size of the area subject to each scan.

As discussed above, position relaxation may be used to better facilitate such comparison. As indicated in block 305, the differences between the first and second plot may be compared to those in a database to determine if such differences are due to discrepancies (as opposed to desired aircraft structures). As indicated in block 306, the results of the comparison are displayed or otherwise communicated so that a user may check the aircraft to verify the presence of discrepancies found according to this process and may then remove or fix the discrepancies.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the invention have been described, it will be apparent to those of ordinary skill in the art that other embodiments and implementations are possible within the scope of the invention. Accordingly, the invention is not to be restricted except in light of the attached claims and their equivalents.

The invention claimed is:

1. A method for detecting foreign object debris in an item comprising:
   directing, with an emitter of a scanner system, an x-ray fan beam at the item during a scan along a single scan axis, wherein the x-ray fan beam is oriented along an axis that is orthogonal to the single scan axis, and wherein the x-ray fan beam penetrates the item and a portion of energy from the x-ray fan beam is backscattered from the item;
   detecting, with a detector of the scanner system, energy intensities of the portion of the energy from the x-ray fan beam backscattered from the item while scanning along the single scan axis;
   forming, with an image-former, a one-dimensional image of the item, wherein the one-dimensional image includes a correspondence between a plurality of different points along the single scan axis and the energy intensities detected at each of the plurality of different points along the single scan axis; and
   comparing, with a comparator, the one-dimensional image with a reference one-dimensional image to determine whether foreign object debris is present behind or within the item, wherein the comparing includes determining a difference between each point of the reference image and a corresponding different point of the plurality of different points along the single scan axis.

2. The method of claim 1, wherein the one-dimensional image is a detected wave intensity plot.

3. The method of claim 1, wherein the detecting the reflected energy waves from the item along the at least one dimension further comprises detecting the backscattered X-rays with a one-dimensional backscatter X-ray scanner.

4. The method of claim 1, wherein the comparing the one-dimensional image of the item with the reference image further comprises subtracting the reference image from the one-dimensional image to form a subtracted image.

5. The method of claim 1, wherein the reference image comprises a second one-dimensional image of the item without the foreign object debris or of a model of the item without the foreign object debris.

6. The method of claim 1, further comprising subjecting the item to a modification, forming the reference image of the item before the modification, and forming the one-dimensional image of the item after the modification.

7. The method of claim 1, wherein the item comprises an aircraft panel having foreign object debris located behind or within the aircraft panel, and further comprising determining that the foreign object debris is present behind or within the item based on the one-dimensional image of the item.

8. The method of claim 1, further comprising using a linear motion device to direct the energy waves at the item along the single scan axis.

9. A system for detecting foreign object debris in an item, the system comprising:
   an emitter configured to emit an x-ray fan beam at an item during a scan along a single scan axis, wherein the emitter includes an x-ray tube with a rectangular slit oriented along an axis perpendicular to the single scan axis, and wherein the x-ray fan beam penetrates the item and the item is configured to backscatter a portion of energy from the x-ray fan beam;
   a detector configured to detect energy intensities of the portion of the x-ray fan beam backscattered from the item while scanning along the single scan axis;
   an image-former configured to form a one-dimensional image of the item, wherein the one-dimensional image includes a correspondence between a plurality of different points along the single scan axis and the energy intensities detected at each of the plurality of different points along the single scan axis; and
   a comparator configured to compare the one-dimensional image of the item with a reference one-dimensional image to determine whether foreign object debris is present behind or within the item, wherein the comparing includes determining a difference between each point of the reference image and a corresponding different point of the plurality of different points along the single scan axis.

10. The system of claim 9, wherein the image-former is configured to form a detected wave intensity plot.

11. The system of claim 9, further comprising a database, accessible by the comparator, of known characteristics of the foreign object debris.

12. The system of claim 9, further comprising a linear motion device which is configured to move at least one of: the emitter and the detector.

13. A software product for detecting foreign object debris in an item, the software product including computer program instructions stored on a non-transitory computer-readable medium, which when the computer program instructions are executed by a processor cause the processor to perform operations, the operations comprising:

directing, with an emitter of a scanner system, an x-ray fan beam at the item during a scan along a single scan axis, wherein the x-ray scan beam is oriented along an axis perpendicular to the single scan axis, and wherein the x-ray fan beam penetrates the item and a portion of energy from the x-ray fan beam is backscattered from the item;

detecting, with a detector of a scanner system, energy intensities of the portion of the x-ray fan beam backscattered from the item while scanning along the single scan axis;

generating, with an image processor, a one-dimensional image of the item, wherein the one-dimensional image includes a correspondence between a plurality of different points along the single scan axis and the energy intensities detected at each of the plurality of different points along the single scan axis; and comparing, with a comparator, the one-dimensional image with a reference one-dimensional image to determine whether foreign object debris is present behind or within the item, wherein the comparing includes determining a difference between each point of the reference image and a corresponding different point of the plurality of different points along the single scan axis.

14. The software product of claim 13, wherein the operations further comprise moving, with a linear motion device, at least one of: the emitter and the one-dimensional detector.

* * * * *